United States Patent [19]

Mashiko

[11] Patent Number: 5,378,492
[45] Date of Patent: Jan. 3, 1995

[54] LATENT FINGERPRINT DETECTION METHOD

[76] Inventor: Kenzo Mashiko, 1097-17, Horicho, Mito-shi, Ibaraki-ken, Japan

[21] Appl. No.: 132,354

[22] Filed: Oct. 6, 1993

[30] Foreign Application Priority Data

Oct. 12, 1992 [JP] Japan .................................. 4-299198

[51] Int. Cl.6 .............................................. A61B 5/117
[52] U.S. Cl. ....................................... 427/1; 427/145; 427/248.1
[58] Field of Search ......................... 427/1, 145, 248.1

[56] References Cited

U.S. PATENT DOCUMENTS 3,075,852 1/1963 Bonora ..................................... 427/1
4,262,623 4/1981 Smith et al. .............................. 427/1

Primary Examiner—Janyce Bell
Attorney, Agent, or Firm—Wegner, Cantor, Mueller & Player

[57] ABSTRACT

A latent fingerprint detection method including dipping latent fingerprints in a solution, the solution including a ruthenium tetroxide and a solvent including a halogen-containing hydrocarbon and/or a halogen-containing ester compound, the solution being prepared by dissolving the ruthenium tetroxide in the solvent; or exposing latent fingerprints to a vapor generated from a solution, the solution including a ruthenium tetroxide and a solvent including a halogen-containing hydrocarbon and/or a halogen-containing ether compound, the solution being prepared by dissolving the ruthenium tetroxide in the solvent.

18 Claims, No Drawings

LATENT FINGERPRINT DETECTION METHOD

FIELD OF THE INVENTION

The present invention relates to a novel method for detecting latent fingerprints using ruthenium tetroxide More particularly, the present invention relates to a latent fingerprint detection method which is free from problems in the environmental hygiene. Accordingly, the present invention can be used for the criminal investigation.

BACKGROUND OF THE INVENTION

Ruthenium tetroxide ($RuO_4$) is reduced to rethenium oxide with a low valence and becomes black when brought into contact with organic materials, particularly oils. For this nature, when brought into contact with latent fingerprints, ruthenium tetroxide comes into contact with oils and fats, or proteins contained in organic materials in the fingerprints, and is converted into ruthenium oxide with a low valence, whose color becomes black, and is attached to the latent fingerprints. Therefore, one can distinctively detect the finger mark of the fingerprint.

Ruthenium tetroxide is a solid having a melting point of 25.5° C. and a boiling point of 100.8° C., readily volatile at normal temperature, and is soluble in water at about 2%. Ruthenium tetroxide dissolved in water is liable to be rapidly reduced to ruthenium oxide with a low valence. Accordingly, since it is difficult to stably store an aqueous solution of ruthenium tetroxide over a long period of time, in practice, it is substantially impossible to use the aqueous solution of ruthenium tetroxide as a detector solution of latent fingerprints.

As conventional methods using ruthenium tetroxide for detecting fingerprints, there is a technology described in Robert D. Olsen, Sr., *Scott's Fingerprint Mechanics*, p. 309 (1978), published by Charles C. Thomas Publisher. Springfield, Ill., U.S.A. The technology described in this literature is a method in which solid ruthenium tetroxide per se is heated on a water bath to vaporize the ruthenium tetroxide, or while utilizing the property of ruthenium tetroxide that it is slightly soluble in water, a ruthenium tetroxide gas generated from its aqueous solution is brought into contact with fingerprints. However, in the above-described direct use method, the temperature at heating on the water bath is limited to not higher than 122° F. (50° C.), and if the heating is carried out at temperatures higher than this temperature, there is a fear of explosion. Also, in the aqueous solution method, it is described that it takes a long period of time to obtain even indistinct fingerprint images because the amount of the generated gas is low. In any of these methods, it is extremely difficult to deal with ruthenium tetroxide, and it is mentioned that these methods must be used only by qualified persons in the laboratories. Hence, these methods have not yet been put into practical uses.

As described above, since it is substantially impossible to practice the use of ruthenium tetroxide which have already been produced for detecting latent fingerprints on the spot of the criminal investigation, a method for detecting latent fingerprints was invented by the present inventors for the purpose of practicing the use on the spot of the criminal investigation and said method has been published (see Japanese Patent Laid-Open No. 3-29642). The gist of this latent finger print detection method is to bring a ruthenium tetroxide gas in the nascent state into contact with latent fingerprints. The method described in the above-described publication as a specific method for using a ruthenium tetroxide gas in the nascent state comprises mixing an aqueous solution of ruthenium chloride with an aqueous solution of ceric ammonium nitrate. However, the above-described method also involves some defects as described below.

(1) The two kinds of the aqueous solutions must be carried to the spot of the fingerprint detection.
(2) The two kinds of the aqueous solutions must be mixed with each other on the spot of the fingerprint detection.
(3) In many cases, the range (area) with which the ruthenium tetroxide gas is brought into contact must be limited.
(4) In the case that the ruthenium tetroxide gas is brought into contact with a wider area, large quantities of the two kinds of the solutions to be mixed must be used so that the method lacks in simplicity.

SUMMARY OF THE INVENTION

An object of the present invention is to provide a fingerprint detection method which can eliminate the defects of the conventional technologies using ruthenium tetroxide, simply operable with safety, and is free from problems in the environmental hygiene.

DETAILED DESCRIPTION OF THE INVENTION

In order to solve the above-described problems, the present inventors have continued investigations and attained this object, to thereby propose the present invention. The novel method for the latent fingerprint detection according to the present invention comprises dipping latent fingerprints in a solution of ruthenium tetroxide in a halogen-based saturated hydrocarbon, an ester, or an ether compound, or exposing said latent fingerprint to its vapor (atmosphere).

As described above, although ruthenium tetroxide is liquefied at around 25° C. and vaporized at around 100° C., as shown in the working examples (practicing at room temperature) of Japanese patent Laid-Open No. 3-29642 or in said Olsen method (heating at 50° C. or lower), a part of ruthenium tetroxide is vaporized even at around room temperature so that it is possible to detect latent fingerprints.

Furthermore, in Japanese Patent Laid-Open No. 3-29642, the detection of latent fingerprints can be carried out by generating (synthesizing) ruthenium tetroxide using a dilute aqueous solution of a compound as the raw material.

This suggests that even if a solution of ruthenium tetroxide is used, or ruthenium tetroxide which is vaporized at around room temperature is used, it is possible to detect latent fingerprints.

On the other hand, although ruthenium tetroxide is soluble in not only water but also many organic solvents, its solution is extremely unstable so that, for example, an aqueous solution thereof is reduced after several tens seconds to ruthenium oxide with a lower valence, whereby the ability for detecting the latent fingerprints is lost. Also, the usual organic solvents exhibit the same behavior so that they can not be used for the object of the present invention.

Thus, there have been extensive investigations in order to call for solvents in which ruthenium tetroxide is stable over a long period of time (at least several months) and is properly soluble in a concentration with which the detection of latent fingerprints can be carried out. As a result, it has been found that halogen-containing saturated hydrocarbons or ether or ester compounds alone or mixtures thereof are extremely suitable for this object, leading to the present invention.

As the halogen-containing saturated hydrocarbons, saturated hydrocarbons having from 1 to 8 carbon atoms and a straight or branched chain structure in which halogen atoms or hydrogen atoms are bonded to the carbon atoms and containing a halogen atom such that the constructional ratio of halogen atoms to hydrogen atoms is 5:5 or more, and preferably 7:3 or more, are suitable.

As the halogen atom in the halogen-containing saturated hydrocarbon, iodine is not suitable, but bromine, chlorine and fluorine, particularly fluorine, are suitable. However, these halogen atoms are not always needed to be present alone, but, for example, compounds having both fluorine and bromine bonded in the molecule can be satisfactorily used as the desired compound.

Specific examples of halogen-containing saturated hydrocarbons which fall within the above-described scope include carbon tetrachloride, trichloromonofluoromethane, dichlorodifluoromethane, dichloromonofluoromethane, monobromotrichloromethane, dibromodichloromethane, tribromomonochloromethane, monobromodichloromonofluoromethane, dibromomonochloromonofluoromethane, tribromomonofluoromethane, monobromotrifluoromethane, monobromodichloromethane, dibromomonochloromethane, tribromomethane, monobromomonochloromonofluoromethane, dibromomonofluoromethane, monobromomonochloromethane, dibromomethane, monobromomonofluoromethane, hexachloroethane, pentachloromonofluoroethane, tetrachloro-1,2-difluoroethane, tetrachloro-1,1-difluoroethane, 1,1,2-trichloromonofluoroethane, 1,1,1-trichlorotrifluoroethane, 1,2-dichlorotetrafluoroethane, 1,1-dichlorotetrafluoroethane, 1,2-dibromotetrafluoroethane, pentachloroethane, 1,1,2,2-tetrachloromonofluoroethane, 1,1,2-trichloro-2,2-difluoroethane 1,2,2-trichloro-1,2-difluoroethane, 1,1,1-trichloro-2,2-difluoroethane, 1,1-dichloro-2,2,2-trifluoroethane, monochloro-1,1,2,2-tetrafluoroethane, 1-chloro-1,1,2,2-tetrafluoroethane, 1,1,2,2-tetrachloroethane, 1,1,1,2-tetrachloroethane, 1,1,2-trichloro-2-fluoroethane, 1,2,2-tetrachloro-2-fluoroethane, 1,2,2-trichloro-2-fluoroethane, 1,1,1-trichloromonofluoroethane, 1,2-dichloro-1,2-difluoroethane, 1,1-dichloro-2,2-difluoroethane, 1,2-dichloro-1,1-difluoroethane, 1,1-dichloro-1,2-difluoroethane, 1-chloro-1,2,2-trifluoroethane, 1-chloro-2,2,2-trifluoroethane, 1-chloro-1,1,2-trifluoro-1,1,2,2-tetrafluoroethane, 1,1,1,2-tetrafluoroethane, 1,2-dichloro-1-fluoroethane, 1-chloro-2,2-difluoroethane, trifluoroethane, hexafluorocyclopropane, 1,1,2,2-tetrachlorotetrafluorocyclobutane, 1,2-dichlorohexafluoro-cyclobutane, monochloroheptafluorocyclobutane, octafluorocyclobutane, 1,2,2-trichloro-3,3,4,4-tetrafluorocyclobutane, 1,1-dichloro-2,2,3,3-tetrafluorocyclobutane, 1-chloro-2,2,3,3-tetrafluorocyclobutane, 1,1,2,2-tetrafluorocyclobutane, hexafluorocyclobutane, hexafluoroheptane, octafluoroheptane, octafluoropentane, decafluorohexane, tetradecafluorohexane, and octafluoroheptane. Also, examples of those having a boiling point of −20° C. or lower include pentafluoroethane, monochloropentafluoroethane, hexafluoroethane, dichlorodifluoromethane, and monochlorodifluoromethane.

Any of these compounds can be used while meeting the object of the present invention. A ruthenium tetroxide solution of a compound having a boiling point of room temperature or lower (about 20° C.) is prepared by cooling a compound as the solvent with a suitable cooling medium (for example, water if the boiling point is up to 30° C., and dry ice-methanol, liquid nitrogen, etc. if the boiling point is 5° C. or lower) to not higher than the boiling point and absorbing ruthenium tetroxide therein. Further, in the case that the ruthenium tetroxide solution in such a low boiling point compound as the solvent is used at normal temperature, the solution is sealed in a pressure vessel and can be used as, for example, an aerosol, etc. while utilizing the vapor pressure of such a solvent at normal temperature, etc. Needless to say, with respect to the above-described halogen-containing saturated hydrocarbons as the solvent of ruthenium tetroxide, only the specific examples thereof have been enumerated, but it should not be construed that the halogen-containing saturated hydrocarbons which can be used in the present invention are limited thereto.

As the ether compounds, halogen-containing ether compounds having from 2 to 10 carbon atoms and containing a halogen atom such that the constructional ratio of halogen atoms to hydrogen atoms bonded to the carbon atoms is 5:5or more are suitable, and specific examples thereof include bis (2,2,2-trifluoroethyl) ether, bis(2-chloro-1,1,2-trifluoroethyl) ether, 2-chloro-1,1,2-trifluoromonofluoromethyl ether, bis(hexachlorobutyl) ether, tetrachloro-1-bromotetrachloroether, and bis(-hexafluoroisopropyl) ether.

As the ester compounds, halogen-containing ester compounds derived from acids such as dichloroacetic acid, monochloroacetic acid, trichloroacetic acid, dibromoacetic acid, difluoroacetic acid, and trifluoroacetic acid and halogen-containing alcohols (such as hexafluoroisopropanol, trifluoroethanol, pentachloropropanol, tetrafluoropropanol, and hexafluorobutanol) can be used.

Needless to say, with respect to these ether and ester compounds, only the typical specific examples thereof which can be used in the present invention have been enumerated, but it should not be construed that the ether and ester compounds which can be used in the present invention are limited thereto.

In the case that these compounds are used as the solvent of ruthenium tetroxide, as a matter of course, these compounds can be used alone, but mixtures such as a mixture of trichloromonofluoromethane and 1,1,2-trichloro-2,2-difluoroethane, a mixture of monobromodichloromonofluoromethane and trichlorotrifluoroethane, and a mixture bis(2,2,2-tri-fluoroethyl) ether and dibromodifluoromethane can also be used.

As described above, while the typical examples of the compounds which can be used as the solvent of ruthenium tetroxide in the present invention have been enumerated use of many of these compounds has limited possibilities because of toxicity to human bodies, such use being taken as a prime mover of getting the natural environment worse. Accordingly, needless to say, in the case that the present invention is commercialized, it is necessary to use compounds (solvents B) while taking these trends into full account.

In the present invention, as the solvent of ruthenium tetroxide, the compounds falling within the specific scope have been appointed among a large number of compounds. This is because many compounds other than those not appointed in the present invention do not dissolve ruthenium tetroxide therein, or even though compounds dissolve ruthenium tetroxide therein, after several seconds or even after several days, their solutions become black or form precipitates so that a ruthenium tetroxide solution which is stable over a long period of time can not be obtained.

As described above, the present invention is applied to the detection of latent fingerprints by dipping in a ruthenium tetroxide solution without any heating or vaporizing (gasifying) ruthenium tetroxide, while utilizing the solubility of ruthenium tetroxide in halogen-containing saturated hydrocarbons or ester or ether compounds, the stability of the solution thereof, and the vaporization of the ruthenium tetroxide solution.

As the gasification method of the ruthenium tetroxide solution, while methods in which the ruthenium tetroxide solution is allowed to merely stand while the vessel (having the solution charged thereinto) is opened, or the solution is charged into a petri dish or the like and allowed to merely stand, are applicable, in order to make the gasification easier, a method in which the solution is dipped in a porous substance having a large surface area such as sponge and gauze (and the surface area is further widened) and allowed to stand, and a method in which the solution is sprayed in a spray state by means of a sprayer, can be applied.

As the porous substance, Teflon-made sponges and ceramic (glass)-made porous materials can be used. Also, these porous substances can be molded into a fabric state, a corrugated state, or into a honeycomb state and then used. A method in which such a porous substance is dipped in the ruthenium tetroxide solution, allowed to stand, and then further positively blown with air to accelerate the vaporization rate, is also applicable.

As the spraying method, a nebulizer mode and a mode using pressurization can be used. As the pressurization mode, there are various methods such as a mode in which a gas such as nitrogen, air, and carbon dioxide is compressed, the pressure of which is used, and a so-called aerosol mode in which a vaporization pressure of a low boiling point compound such as lower fluorohydrocarbon compounds is used.

However, with respect to the above-described various methods, while only the examples for rapidly vaporizing ruthenium tetroxide (solution) in a wide range have been described, it should not be construed that the present invention is limited to these various methods. Any methods can be applied if the ruthenium tetroxide solution can be vaporized in a wide range within a short period of time by a simple and easy operation mode depending on the case where the detection of fingerprints is required.

The capability for detecting (latent) fingerprints according to this mode is extremely high and qualitative. When an artificial lipid (a mixture of 70 parts of ricinoleic acid and 30 parts of gelatin) prepared to imitate fingerprints is dissolved in n-hexane and dropped on a glass filter, and the residue from which the n-hexane has been vaporized is exposed to a gas of ruthenium tetroxide for 5 minutes, the detection can be made to an extent of 0.005 mg of the artificial lipid.

For this reason, in the detection of latent fingerprints, it is not necessary to positively bring the ruthenium tetroxide solution into contact with latent fingerprints (by dipping the latent fingerprints in the solution or sprinkling the solution onto the latent fingerprints), but it is possible to visualize the latent fingerprints only by exposing (by allowing to stand) the latent fingerprints to a gas (vapor) of the ruthenium tetroxide solution.

However, in practice, in order to distinctly detect fingerprints at lower densities within a shorter period of time, a method in which an instrument having latent fingerprints attached thereto is allowed to stand in an atmosphere filled with a ruthenium tetroxide solution gas (such as, for example, a desiccator having a ruthenium tetroxide solution charged in the lower part thereof, plastics having charged therein small pieces of a Teflon-made sponge dipped in a ruthenium tetroxide solution, e.g., polyethylene-made packs, polyvinylidene chloride-made packs, Teflon-made packs, etc.), and a method in which a part having fingerprints attached thereto is covered by a plastic-made film, etc. and then (internally) sprayed with a ruthenium tetroxide solution, are extremely effective. However, with respect to the detection method, there is no definite method, but more appropriate methods may be employed depending on the place where the detection of fingerprints is required, the type of environment (of an instrument), etc.

On the other hand, since in practice, not only latent fingerprints but also many organic substances are visualized at the same time, the attachment of other organic substances in the vicinity of the latent fingerprints results in contamination of the "fingerprints". Such unnecessary and excessive contaminated black materials can readily be decolorized by bringing into contact with an oxide (aqueous) solution of an alkali metal or alkaline earth metal salt of perchloric acid, hypochlorous acid, periodic acid, perboric acid, etc.

This removal method of (black) contaminants can similarly be used for not only the removal of contaminants in the vicinity of the latent fingerprints but also the removal of contaminants in vessels, detection instruments, clothings, skins, etc.

Specific examples of the method for preparing a ruthenium tetroxide solution are given below. The method includes the following three methods.

(1) A ruthenium tetroxide solid is dissolved in a solvent.
(2) Ruthenium tetroxide is generated (synthesized) and absorbed in a solvent.
(3) The generation and absorption of ruthenium tetroxide are carried out at the same time in the same instrument.

Needless to explain, in the method (1), ruthenium tetroxide (which is a reagent in a solid state) is dissolved in the solvent as specified in the specification of the present application, and the ruthenium tetroxide is expensive and requires a strict care in the treatment thereof.

The method (2) is classified into the following two methods depending on the generation manner of ruthenium tetroxide (in a gas state).

(A) A solid of ruthenium tetroxide is heated on a water bath to form a gas, which is then introduced into a solvent and absorbed (dissolved) therein.
(B) A ruthenium aqueous solution (such as, for example, a ruthenium chloride aqueous solution and a ruthenium nitrate aqueous solution) is mixed with a ceric ammonium nitrite aqueous solution to generate ruthenium tetroxide, the gas of which is then introduced into a solvent and absorbed therein. Also, as described above, depending on the boiling point of the solvent, the absorption method requires or does not require the cooling.

In the methods (A) and (B), if the treatment is carried out in a closed system and practiced in a dry air stream, and the generated ruthenium tetroxide is introduced together with the air stream into the solvent, a ruthenium tetroxide solution can be obtained easily and effectively.

In the method (3), in the case that the compound to be used as the solvent is insoluble in water, necessary amounts of a ruthenium salt aqueous solution and a ceric ammonium nitrate aqueous solution are added to the solvent, the mixture is further mixed to thereby react the ruthenium salt with ceric ammonium nitrate, and ruthenium tetroxide is generated and simultaneously absorbed (migrated) in the solvent to form a solution. While the above-described three methods have been described as typical examples for preparing a ruthenium tetroxide solution, needless to say, it should not be limited that the preparation method of the solution is limited to the above-described methods.

The ruthenium tetroxide solution using, as a solvent, the compound as specified in the present invention can be stored at room temperature over a long period of time without causing changes under the usual condition in a dark place. However, the solution is possibly blackened upon contact with a moisture or by the action of walls of a storage vessel, etc. As a result of investigations in order to prevent this blackening phenomenon from occurrence, it has been found that the blackening phenomenon can be prevented if ceric ammonium nitrate is added in an amount of from 0.05 to 5% by weight to the ruthenium tetroxide solution. In other words, it has been found that the above-ceric ammonium nitrate or the like serves as a stabilizer for ruthenium tetroxide and will be an extremely important additive in commercialization of the ruthenium tetroxide solution.

As described above, if a ruthenium tetroxide-containing solution (gas) is brought into contact with (latent) fingerprints, the ruthenium tetroxide is reduced and blackened by organic substances present in the fingerprints, the latent fingerprints are rapidly visualized, and at the same time, the halogen-containing saturated hydrocarbon or ester or ether compound used as the solvent (for ruthenium tetroxide) is removed without contaminating the visualized fingerprints.

According to the method of the present invention, the following effects can be brought.

When latent fingerprints are dipped in a solution of ruthenium tetroxide in a halogen-containing saturated hydrocarbon or ester or ether compound alone or in admixture, or exposed to a vapor thereof, distinct fingerprint images can be obtained within a short period of time.

Many of the solvents for ruthenium tetroxide as specified in the present invention are non-flammable, and compounds which are quite less in toxicity are included. If such a compound is selected, a ruthenium tetroxide solution which is stable and non-toxic can be obtained.

When a porous substance is dipped in or sprayed with a ruthenium tetroxide solution, the ruthenium tetroxide can be gasified without heating.

Distinct fingerprint images can be obtained without influencing a substance (material) to which latent fingerprints are attached.

A ruthenium tetroxide solution can be obtained by dissolving a solid of ruthenium tetroxide in a solvent, absorbing (dissolving) its gas in a solution, or by further reacting ruthenium chloride with a ceric ammonium nitrate aqueous solution in a solvent.

If ceric ammonium nitrate is added to a ruthenium tetroxide solution, the ruthenium tetroxide solution can be stabilized.

The contamination by a ruthenium tetroxide solution can readily be eliminated upon contact with an inorganic oxidizer aqueous solution.

Fingerprint images are black, and minute parts thereof can be detected.

When an instrument to which latent fingerprints are attached is received in an airtight container, or covered by a plastic film, and exposed to a ruthenium tetroxide vapor, more distinct fingerprint images are obtained within a short period of time.

Latent fingerprints in a closed space such as those in automobiles or room can also be detected.

The present invention will be described below with reference to the following examples. It should not be construed that the present invention is limited thereto.

EXAMPLE 1

(A) Preparation of Latent Fingerprint Samples (A-1) Latent fingerprint on paper:
The tip of an index finger of a right hand was pressed at a pressure of about 500 g on a dry type copying paper, to prepare a latent fingerprint sample on paper.

(A-2) Latent fingerprint on glass:
A tole-type beaker having an internal volume of 200 ml was charged with 100 ml of water and lifted by a right hand to a height of the breast for 10 seconds, to prepare a latent fingerprint on glass.

(A-3) Latent fingerprint on ceramic:
A white (ceramic-made) cup having an internal volume of about 200 ml was charged with 100 ml of water and lifted by a right hand to a height of the breast for 10 seconds, to prepare a latent fingerprint on ceramic.

(A-4) Latent fingerprint on metal:
The tip of an index finger of a right hand was pressed at a pressure of about 500 g on a stainless steel plate (SAS-18), to prepare a latent fingerprint sample on metal.

(B) preparation of Ruthenium Tetroxide Solutions (B-1) A three-necked flask having an internal volume of 500 ml is installed with an inlet (glass) tube for air, an outlet (glass) tube for a ruthenium tetroxide gas (a mixed gas with air) (generated upon the reaction), and a dropping funnel, 100 ml of a 0.5% aqueous solution of ruthenium chloride (a guaranteed reagent) and a Teflon-coated stirrer are then charged therein, and the flask is set on a magnetic stirrer. Air is introduced at a flow rate of 300 m/min. into the flask while stirring the contents, and the air is discharged outside through a Muenke scrubbing bottle having 100 ml of a ruthenium tetroxide absorption solution filled therein, installed at the tip of the outlet (for the ruthenium tetroxide gas).

150 ml of a 4% aqueous solution of ceric ammonium nitrate (a guaranteed reagent) is added dropwise from the dropping funnel over 10 minutes. Ruthenium tetroxide is generated at the same time of the dropwise addition, and the absorption solution is changed yellow. After completion of the addition of the whole content of the ceric ammonium nitrate aqueous solution, the operation is continued for an additional 10 minutes, to prepare a ruthenium tetroxide solution.

The ruthenium tetroxide solution obtained by this reaction is added with 10 g of anhydrous sodium sulfate and dried thereover at room temperature for 24 hours, to obtain a ruthenium tetroxide solution.

(B-2) A dropping funnel having an internal volume of one liter is charged with 500 m of a ruthenium tetroxide absorption solution and further added with 100 ml of a 1.0% ruthenium chloride aqueous solution and 100 ml of a 5.0% ceric ammonium nitrate aqueous solution, and after plugging, the contents are vigorously shaken for 10 minutes. After allowing to stand, the contents are separated into two layers. The lower layer absorption solution is changed yellow. The lower layer solution is separated and dispensed in a 2-liter three-necked flask.

To the upper layer (aqueous) solution left in the funnel. 200 ml of the absorption solution (the same as above) and 50 ml of a ceric ammonium nitrate aqueous solution are added, and the same treatment as described above is carried out, to obtain a pale yellow absorption solution.

After adding the lower layer absorption solution to the above-described absorption solution, the mixed absorption solution is dried over anhydrous sodium sulfate, to obtain a ruthenium tetroxide solution.

Detection of Latent Fingerprints 3,3-dichloro-1,1,1,2,2-pentafluoropropane is used as an absorption solution, 20 m of the ruthenium tetroxide solution prepared in the method (B-2) is poured into a lower part of a desiccator having an internal volume of about five liters, a ceramic-made base plate is charged therein, each of the samples (A-1) (latent fingerprints on paper), (A-2) (latent fingerprints on glass), (A-3) (latent fingerprints on ceramic), and (A-4) (latent fingerprints on metal) is placed thereon, and the desiccator is lidded. Several seconds after the lidding, the latent fingerprints become appeared as black fingerprint images. After five minutes, the desiccator is opened, the samples (A-1) to (A-4) are discharged out. In each of the samples, extremely distinct black fingerprint images appear.

EXAMPLE 2

The ruthenium tetroxide solution used in example 1 was diluted with a two-fold amount of dichloropentafluoropropane, and the detection of latent fingerprints was carried out in the same manner as in Example 1 with respect to the same samples. While the degree of blackening of the fingerprints was slightly lowered as compared with that in Example, black images having a density sufficient for the measurement of fingerprints were obtained.

EXAMPLE 3

A ruthenium tetroxide solution is prepared in the same manner as in the method (B-1), except for using monobromodichloromonofluoromethane as the absorption solution. 2 ml of this solution is charged in a standard type nebulizer, and air is introduced thereinto, to generate a spray of the ruthenium tetroxide solution. On the other hand, the sample (A-2) is charged in a polyvinylidene chloride-made bag having an internal volume of two liters, the mouth of the bag is tightened, the tip of the nebulizer is inserted into the bag, and the spray is sprayed for 2 seconds. At this time, a care is taken such that the sample (A-2) is not splashed directly with the spraying solution. Black fingerprint images appear on the sample substantially simultaneously with the spraying. Three minutes after the spraying, the mouth of the bag is closed, and the sample is then discharged from the bag. Five extremely distinct fingerprint images appear on the beaker.

EXAMPLE 4

A ruthenium tetroxide solution is prepared in the same manner as in the method (B-2), except for using a mixed solution of 30 parts of carbon tetrachloride and 70 parts of trichloromonofluoromethane as the absorption solution. 1.5 ml of this solution is dropped on and dipped in a Teflon-made sponge (thickness: 5 mm, width: 10 mm, length: 15 mm). On the other hand, the samples (A-1), (A-3) and (A-4) are placed on a glass plate, the whole is covered by a Teflon-made film, and a ruthenium tetroxide-dipped sponge is charged therein, followed by a allowing to stand for 10 minutes. Meanwhile, a care is taken such that the terminal portion of polyvinylidene chloride is brought into intimate contact with the glass plate and that the ruthenium tetroxide solution does not leak out from this terminal portion. After ten minutes, distinct black fingerprint images appear in each of the samples. In the samples taken out one minute after the treatment under the same conditions, though fingerprint images appeared, the degree of blackening was so low that the determination of fingerprint images was slightly difficult. In particular, in the sample (A-1), this tendency was strongly noted.

EXAMPLE 5

A ruthenium tetroxide solution is prepared in the same manner as in the method (B-1), except for using a mixed solution of 10 parts of hexafluoropropyl ester monofluoroacetate and 90 parts of 1,1,2-trichloro-1,2,2-trifluoroethane as the absorption solution. 5 ml of this solution is charged in a piston type sprayer (comprising a glass-made solution container and a stainless steel-made spraying part) and sprayed on a glass vessel having an internal volume of about 15 liters and having the samples (A-1) to (A-4) charged therein (a water tank for tropical fishes lidded with a glass plate) for 3 seconds (amount of the solution: about 1.5 ml). While black fingerprints appear substantially simultaneously with the spraying, after the spraying, the glass vessel is lidded with the glass plate and allowed to stand for 5 minutes. In each of the samples taken out from the glass vessel, extremely distinct black fingerprint images appeared.

EXAMPLE 6

A ruthenium tetroxide solution prepared in the same manner as in the method (B-2), except for using a mixed solution of 10 parts of bis(2,2,2-trifluoro) ether and 90 parts of 1,1-dichloro-1,2,2-trifluoroethane as the absorption solution, was stabilized by the addition of a fine powder of ceric ammonium nitrate in an amount of 0.5% (a weight ratio to the solution). On the other hand, the samples (A-1) to (A-4) were placed on a plastic plate which had been placed a rear seat of an automobile, "Crown" manufactured by Toyota Motor Corporation, and after closing all doors, part of the doors were opened. About 10 ml of the ruthenium tetroxide solution was sprayed into the automobile by means of a pressure type sprayer, and the doors were closed, followed by allowing to stand for 20 minutes. Thereafter, the doors of the automobile were opened, and the samples were taken out to confirm the appearance of fingerprint images. As a result, in each of the samples, fingerprint images appeared at densities sufficient for the determination of fingerprints. Incidentally, a steering wheel, an armrest, window shields, meter covers, etc., to which substances similar to the fingerprints appear to have been attached, were contaminated black by the spraying of the ruthenium tetroxide solution, similar to the fingerprints. However, this contamination could easily be eliminated by wiping with a cloth dipped with a 3% sodium hypochlorite aqueous solution, etc.

While the invention has been described in detail and with reference to specific embodiments thereof, it will be apparent to one skilled in the art that various changes and modifications can be made therein without departing from the spirit and scope thereof.

What is claimed is:

1. A latent fingerprint detection method comprising:
   A. dipping latent fingerprints in a solution, said solution comprising a ruthenium tetroxide and a solvent comprising a halogen-containing hydrocarbon having 1-8 carbons, the ratio of halogen atoms to hydrogen atoms in said halogen-containing hydrocarbon being 5:5 or more, said solution being prepared by dissolving said ruthenium tetroxide in said solvent; or
   B. exposing latent fingerprints to a vapor generated from a solution, said solution comprising a ruthenium tetroxide and a solvent comprising a halogen-containing hydrocarbon having 1-8 carbons, the ratio of halogen atoms to hydrogen atoms in said halogen-containing hydrocarbon being 5:5 or more, said solution being prepared by dissolving said ruthenium tetroxide in said solvent.

2. A latent fingerprint detection method as claimed in claim 1, wherein said ruthenium tetroxide is a ruthenium tetroxide solid and said solution is prepared by dissolving said ruthenium tetroxide solid in said solvent.

3. A latent fingerprint detection method as claimed in claim 1, wherein said ruthenium tetroxide is a ruthenium tetroxide gas and said solution is prepared by dissolving said ruthenium tetroxide gas in said solvent.

4. A latent fingerprint detection method as claimed in claim 1, wherein said solution is prepared by mixing said solvent with a ruthenium compound and a ceric ammonium nitrate, and said mixing of said solvent with said ruthenium compound causes a synthesis of said ruthenium tetroxide.

5. A latent fingerprint detection method as claimed in claim 4, wherein said solution is prepared by mixing said solvent with from 0.05% to 5% by weight of said ceric ammonium nitrate aqueous solution and said ruthenium compound is a ruthenium salt.

6. A latent fingerprint detection method as claimed in claim 1, wherein said vapor generated from said solution includes said ruthenium tetroxide and the generation of said vapor is carried out by spraying said solution.

7. A latent fingerprint detection method as claimed in claim 1, wherein contamination of said solution is inhibited by using an inorganic oxidizer aqueous solution.

8. A latent fingerprint detection method as claimed in claim 1, wherein an instrument having latent fingerprints attached thereto is received enclosed in an airtight container, or covered by a plastic film, and then exposed to said vapor generated from said solution.

9. A latent fingerprint detection method as claimed in claim 1, wherein said solution further comprises a halogen-containing ether compound having 2-10 carbons, the ratio of halogen atoms to hydrogen atoms in said halogen-containing ether compound being 5:5 or less.

10. A latent fingerprint detection method comprising:
    A. dipping latent fingerprints in a solution, said solution comprising a ruthenium tetroxide and a solvent comprising a halogen-containing ether compound having 2-10 carbons, the ratio of halogen atoms to hydrogen atoms in said halogen-containing ether compound being 5:5 or more, said solution being prepared by dissolving said ruthenium tetroxide in said solvent; or
    B. exposing latent fingerprints to a vapor generated from a solution, said solution comprising a ruthenium tetroxide and a solvent comprising a halogen-containing ether compound having 2-10 carbons, the ratio of halogen atoms to hydrogen atoms in said halogen-containing ether compound being 5:5 or more, said solution being prepared by dissolving said ruthenium tetroxide in said solvent.

11. A latent fingerprint detection method as claimed in claim 10, wherein said ruthenium tetroxide is a ruthenium tetroxide solid and said solution is prepared by dissolving said ruthenium tetroxide solid in said solvent.

12. A latent fingerprint detection method as claimed in claim 10, wherein said ruthenium tetroxide is a ruthenium tetroxide gas and said solution is prepared by dissolving said ruthenium tetroxide gas in said solvent.

13. A latent fingerprint detection method as claimed in claim 10, wherein said solution is prepared by mixing said solvent with a ruthenium compound and a ceric ammonium nitrate, and said mixing of said solvent with said ruthenium compound causes a synthesis of said ruthenium tetroxide.

14. A latent fingerprint detection method as claimed in claim 12, wherein said solution is prepared by mixing said solvent with from 0.05% to 5% by weight of said ceric ammonium nitrate aqueous solution and said ruthenium compound is a ruthenium salt.

15. A latent fingerprint detection method as claimed in claim 10, wherein said vapor generated from said solution includes said ruthenium tetroxide and the generation of said vapor is carried out by spraying said solution.

16. A latent fingerprint detection method as claimed in claim 10, wherein contamination of said solution is inhibited by using an inorganic oxidizer aqueous solution.

17. A latent fingerprint detection method as claimed in claim 10, wherein an instrument having latent fingerprints attached thereto is received enclosed in an airtight container, or covered by a plastic film, and then exposed to said vapor generated from said solution.

18. A latent fingerprint detection method as claimed in claim 10, wherein said solution further comprises a halogen-containing hydrocarbon having 1-8 carbons, the ratio of halogen atoms to hydrogen atoms in said halogen-containing hydrocarbon being 5:5 or more.

* * * * *